(12) United States Patent
Pan et al.

(10) Patent No.: US 6,322,509 B1
(45) Date of Patent: Nov. 27, 2001

(54) METHOD AND APPARATUS FOR AUTOMATIC SETTING OF SAMPLE GATE IN PULSED DOPPLER ULTRASOUND IMAGING

(75) Inventors: Lihong Pan, Brookfield; Larry Y. L. Mo, Waukesha; Michael J. Washburn, New Berlin; Fang Dong, Middleton, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/656,659

(22) Filed: Sep. 7, 2000

Related U.S. Application Data

(63) Continuation-in-part of application No. 09/563,538, filed on May 1, 2000.

(51) Int. Cl.⁷ ..................... A61B 8/00
(52) U.S. Cl. ............... 600/443; 600/447
(58) Field of Search .............. 600/443, 447, 600/444, 449, 437; 382/294; 601/7

(56) References Cited

U.S. PATENT DOCUMENTS

| | | | |
|---|---|---|---|
| 4,937,797 | 6/1990 | Snyder et al. | 367/138 |
| 5,365,929 | 11/1994 | Peterson | 128/661.1 |
| 5,623,930 * | 4/1997 | Wright et al. | 600/443 |
| 5,690,116 | 11/1997 | Goujon | 128/661.08 |
| 6,068,598 | 5/2000 | Pan et al. | 600/453 |

FOREIGN PATENT DOCUMENTS

| 0842638 | 5/1998 | (EP) . |
|---|---|---|
| 0985380 | 3/2000 | (EP) . |

* cited by examiner

*Primary Examiner*—Marvin M. Lateef
*Assistant Examiner*—Maulin Patel
(74) *Attorney, Agent, or Firm*—Peter J. Vogel; Dennis M. Flaherty

(57) ABSTRACT

A method and an apparatus for automatically initializing and adjusting the Doppler sample gate position and size settings based on actual vessel image data. A vessel segment search method employs an object search technique based solely on geometric and morphological information in a binarized vessel image obtained from either B-mode or color flow image data. The morphologically best or nearest vessel segment within a target search region in the two-dimensional image is found. The sample gate is placed at or near the center of the targeted vessel segment. The sample gate size is adjusted in relation to the vessel size. Then the best available steering angle that minimizes the Doppler angle is selected.

37 Claims, 7 Drawing Sheets

METHOD AND APPARATUS FOR AUTOMATIC SETTING OF SAMPLE GATE IN PULSED DOPPLER ULTRASOUND IMAGING

RELATED PATENT APPLICATION

This application is a continuation-in-part application claiming priority from U.S. patent application Ser. No. 09/563,538 filed on May 1, 2000.

FIELD OF THE INVENTION

This invention generally relates to the imaging of moving ultrasound scatterers. In particular, the invention relates to methods for positioning the gate or sample volume (hereinafter "sample gate") in medical diagnostic ultrasound imaging.

BACKGROUND OF THE INVENTION

Premium medical diagnostic ultrasound imaging systems require a comprehensive set of imaging modes. These are the major imaging modes used in clinical diagnosis and include timeline Doppler, color flow Doppler, B mode and M mode. In the B mode, such ultrasound imaging systems create two-dimensional images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. In the spectral Doppler imaging mode, the power spectrum of these Doppler frequency shifts are computed for visual display as velocity-time waveforms.

One of the primary advantages of Doppler ultrasound is that it can provide noninvasive and quantitative measurements of blood flow in vessels. Given the angle between the insonifying beam and the flow axis (hereinafter referred to as the "Doppler angle"), the magnitude of the velocity vector can be determined by the standard Doppler equation:

$$v = c f_d / (2 f_0 \cos \theta) \quad (1)$$

where c is the speed of sound in blood, $f_0$ is the transmit frequency and $f_d$ is the motion-induced Doppler frequency shift in the backscattered ultrasound signal.

In conventional ultrasound spectral Doppler imaging, the operator is required to manually position the sample gate to the measurement location in a two-dimensional image with or without color flow data. The operator also needs to manually adjust the sample gate size relative to the diameter of the vessel to be studied. From the acoustic data acquired over many transmit firings, Doppler frequency spectral data is obtained via standard Fast Fourier Transform (FFT) spectral analysis.

For a given measured Doppler frequency shift $f_d$, the flow velocity (speed) v is calculated using Eq. (1). The ideal Doppler angle is zero, i.e., when the beam is aligned in the direction of blood flow. Unfortunately, Doppler angles that can be formed in practice tend to be larger, and as they approach 90 degrees, a small error in the angle estimate can lead to a large error in v. For this reason, it is generally recommended that the Doppler beam be steered to form Doppler angles of no greater than about 60 degrees for reliable velocity measurements. Angle steering is another adjustment the operator needs to make manually in conventional Doppler systems.

In an attempt to minimize manual Doppler adjustments when the spectral Doppler mode is activated, conventional scanners generally provide presets for the Doppler sample gate position and size, and for the beam steering angle. However, such presets have limited benefits because the vessel depth, size and orientation relative to the probe can vary a great deal from one case study to the next.

U.S. Pat. No. 5,365,929 describes the use of multiple range gates and multiple Doppler beams to scan a region of interest. By comparing some signal characteristic, such as total power or maximum velocity, of the multiple sample volumes, the scanner automatically selects the best sample gate for full spectral analysis and display. It will appear to the user that the scanner has automatically positioned the sample gate at a location where the Doppler signal is optimal in some sense.

European Patent Application No. 0 842 638 A2 describes a method of tracking vessel walls in the B-mode image, and then automatically adjusting the sample volume size to ensure the entire vessel diameter is covered. While this may be useful for volume flow measurements, the user is still expected to first manually position the sample volume and vessel wall markers at the correct locations. Also, in Doppler exams that do not involve volume flow measurements, different clinics may follow different practices in terms of sample gate size relative to the vessel diameter.

European Patent Application No. 0 985 380 A1 describes a method for automatic positioning of the Doppler sample gate based on bloodstream or color flow information. Among various specific applications, this method can be used to automatically set the sample gate cursor at an optimal position when the sample gate is first brought up in the image, or when it is being moved. The optimal position may be defined by a color flow pixel showing the highest velocity, or the center point of the largest flow segment, or the center point of the next best flow segment etc.

U.S. Pat. No. 5,690,116 describes a method of estimating the orientation (slope) of the vessel axis based on gray-scale image data, and then computing the Doppler angle.

U.S. Pat. No. 6,068,598 describes a robust method for detecting the vessel walls based on B-mode and/or color flow data, estimating the vessel orientation based on the best vessel edge data, and then computing the Doppler angle.

U.S. Pat. No. 4,937,797 describes a method of adjusting the transducer array beamforming delays to automatically steer the Doppler beam to achieve a target Doppler angle such as 60 degrees (or less). This method, however, requires the user to first manually rotate an angle cursor on the B-mode image to define the vessel orientation or flow direction.

There is a need for an automatic method of initializing and adjusting the Doppler sample gate position and size settings and the beam steering angle setting based on actual vessel image data, with the goal of improving the efficiency of the Doppler study above and beyond what can be achieved using presets.

SUMMARY OF THE INVENTION

The present invention is directed to a method and an apparatus which provides automatic initialization and adjustment of the Doppler sample gate position and size settings, and of the beam steering angle setting based on actual vessel image data. This capability is presented as an aid or "smart feature" to the user when either one of the two following conditions is met: (1) when the sample gate cursor is first activated or brought up in the image (before or upon spectral Doppler mode activation); or (2) when the sample gate cursor is being moved. Both of these conditions are normally monitored automatically by the master controller of the system. In accordance with the preferred embodiment of the invention, if either condition is detected, the following functions are automatically performed: (1) the "morphologically best" or nearest vessel segment within a target search region in the two-dimensional image is found; (2) the sample gate is placed at or near the center of the targeted vessel segment; (3) the sample gate size is adjusted in relation to the vessel size; and (4) the best available steering angle that minimizes the Doppler angle is selected. All four features are intended to provide a good but initial adjustment to the sample gate position and size and to the beam steering angle, which should facilitate further manual adjustments by the user. It is not generally possible to predict exactly which vessel or vessel portion the user wants to study, but by setting up the Doppler sampling parameters according to the best image data available, this invention will improve examination speed and/or ease of use.

The vessel segment search method (step 1 above) in accordance with the preferred embodiment of the invention employs an object search technique based solely on geometric and morphological information in a binarized vessel image obtained from either B-mode or color flow image data. The vessel extraction method disclosed herein is not based on comparing Doppler signal characteristics from multiple sample volumes. The method in accordance with the preferred embodiment comprises the following steps: (a) reading an image frame from memory; (b) defining a search region within the image frame or a decimated version of the image frame; (c) binarizing the pixel values within the search region based on a pixel value threshold that is adaptive to local pixel value statistics or based on the presence or absence of color flow information in each pixel; (d) morphological filtering the binarized pixel values to eliminate structures smaller than the speckle size; (e) counting the number of continuous objects and keeping track of their area; (f) rejecting objects that are outside a predetermined size range; and (g) finding the center point of the "best" vessel segment. As a result of this method, the sample gate position can be automatically set.

Having identified the center of the best vessel segment, the vessel diameter and orientation can be computed using any automated method. The sample gate size can then be automatically set to be some fraction of the vessel diameter.

DETAILED DESCRIPTION OF THE PREFERRED EMBODIMENTS

Figure 1:
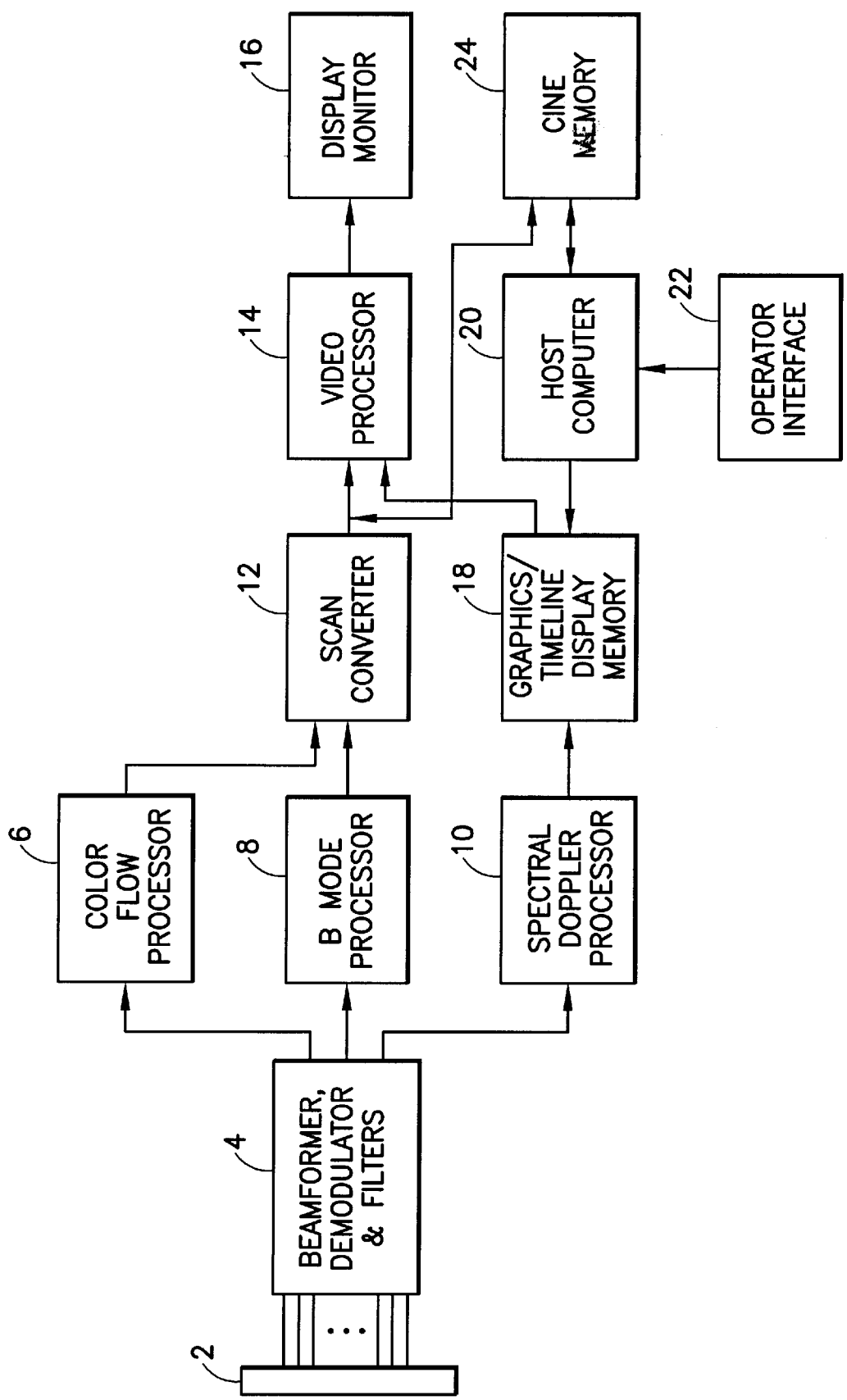
FIG. 1 is a schematic showing a block diagram of a typical ultrasound imaging system which can be programmed with software in accordance with the preferred embodiment of the present invention.

An ultrasound imaging system programmed with software in accordance with the preferred embodiment of the present invention is generally depicted in FIG. 1. The main data path begins with the analog RF inputs to the beamformer board 4 from the transducer 2. The beamformer board 4 is responsible for the transmit and receive beamforming. The beamformer's signal inputs are the low-level analog RF signals from the transducer elements. The beamformer board 4, which comprises a beamformer, a demodulator and filters, outputs two summed digital baseband I and Q receive beams formed from acquired data samples. These data samples are derived from the reflected ultrasound from respective focal zones of the transmitted beams. The I and Q data is sent to FIR filters which are programmed with filter coefficients to pass a band of frequencies centered at the fundamental frequency $f_0$ of the transmit waveform or a (sub)harmonic frequency thereof.

The image data output from the filters is sent to the midprocessor subsystem, where it is processed according to the acquisition mode and output as processed vector data. Typically, the midprocessor subsystem comprises a color flow processor 6, a B-mode processor 8 and a spectral Doppler processor 10. Alternatively, a digital signal processor or array of such processors can be programmed to process signals for all three modes.

The B-mode processor 8 converts the baseband I and Q data from the beamformer board 4 into a log-compressed version of the signal envelope. The B-mode function images the time-varying amplitude of the envelope of the signal as a gray scale. The envelope of a baseband signal is the magnitude of the vector which I and Q represent. The I,Q phase angle is not used in the B-mode display. The magnitude of the signal is the square root of the sum of the squares of the orthogonal components, i.e., $(I^2+Q^2)^{1/2}$. The B-mode intensity data is output to a B-mode acoustic line memory (not shown) in the scan converter 12.

The scan converter 12 accepts the processed B-mode vector data, interpolates where necessary, and converts the data into X-Y format for video display. The scan-converted frames are passed to a video processor 14, which maps the video data to a gray-scale mapping for video display. A conventional ultrasound imaging system typically employs a variety of gray maps, which are simple transfer functions of the raw image data to display gray levels. The gray-scale image frames are then sent to the display monitor 16 for display.

The B-mode images displayed by monitor 16 are produced from an image frame of data in which each datum indicates the intensity or brightness of a respective pixel in the display. An image frame may, e.g., comprise a 256×256 data array in which each intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a plane through the body being imaged.

The color flow processor 6 is used to provide a real-time two-dimensional image of blood velocity in the imaging plane. The frequency of sound waves reflecting from the inside of blood vessels, heart cavities, etc. is shifted in proportion to the velocity of the blood cells; positively shifted for cells moving towards the transducer and negatively for those moving away. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. The color flow processor 6 receives the summed left and right, complex I/Q data from the beamformer board 4 and processes it to calculate the mean blood velocity, variance (representing blood turbulence) and total prenormalization power for all sample volumes within an operator-defined region. These three output values are then combined into two final outputs, one primary and one secondary. The primary output will be either velocity or power. The secondary output can be either variance or power. Which two values will be displayed is determined by the operator-selected display mode. Both values are sent to a color acoustic line memory (not shown) in the scan converter 12. The change or shift in backscattered frequency increases when blood flows toward the transducer and decreases when blood flows away from the transducer. Typically, color flow mode displays hundreds of adjacent sample volumes simultaneously, all laid over a B-mode image and color-coded to represent each sample volume's velocity.

In the color flow mode of the conventional ultrasound imaging system, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilo-hertz range. A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by a beamformer.

For example, the traditional color firing sequence is a series of firings (e.g., tone bursts) along the same position, which firings produce the respective receive signals:

$$F_1 F_2 F_3 F_4 \ldots F_M$$

where $F_1$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point is filtered to produce the respective difference signals:

$$(F_1-F_2)(F_2-F_3)(F_3-F_4) \ldots (F_{M-1}-F_M)$$

and these differences are input to a color flow velocity estimator. Typically, the corner turner memory, wall filter and parameter (e.g., velocity) estimators are incorporated into the color flow processor 6.

The color and B-mode acoustic line memories in scan converter 12 respectively accept processed digital data from the color flow and B-mode processors. These components of the scan converter also perform the coordinate transformation of the color flow and B-mode data from polar coordinate (R-θ) sector format or Cartesian coordinate linear format to appropriately scaled Cartesian coordinate display pixel data, which is stored in an X-Y display memory (not shown) in the scan converter. Color flow images are produced by superimposing a color image of the velocity of moving material, such as blood, over a black and white anatomical B-mode image.

If the image to be displayed is a combination of one B-mode frame and one color flow frame, then both frames are passed to the video processor 14, which maps the B-mode data to a gray map and maps the color flow data to a color map for video display. In the final displayed image, the color pixel data is superimposed on the gray-scale pixel data. Successive frames of color flow and/or B-mode data are stored in a cine memory 24 on a first-in, first-out basis. Storage can be continuous or as a result of an external trigger event. The cine memory 24 is like a circular image buffer that runs in the background, capturing image data that is displayed in real time to the user. When the user freezes the system (by operation of an appropriate device on the operator interface 22), the user has the capability to view image data previously captured in cine memory.

In spectral Doppler imaging, the I/Q components are integrated (summed) over a specific time interval and then sampled by the spectral Doppler processor 10. The summing interval and the transmit burst length together define the length of the sample volume (i.e., sample gate) as specified by the user. A "sum and dump" operation effectively yields the Doppler signal backscattered from the sample volume. The Doppler signal is passed through a wall filter which rejects any clutter in the signal corresponding to stationary or very slow-moving tissue. The filtered output is then fed into a spectrum analyzer, which typically takes Fast Fourier Transforms (FFTs) over a moving time window of 32 to 128 samples. Each FFT power spectrum is compressed and then output by the spectral Doppler processor 10 to a graphics/timeline display memory 18. The video processor 14 maps the compressed spectral Doppler data to a gray scale for display on the monitor 16 as a single spectral line at a particular time point in the Doppler velocity (frequency) versus time spectrogram.

System control is centered in a host computer (i.e., master controller) 20, which accepts operator inputs through an operator interface 22 (e.g., a control panel) and in turn controls the various subsystems. The host computer 20 performs system level control functions. It accepts inputs from the operator via the operator interface 22 as well as system status changes (e.g., mode changes) and makes appropriate system changes. A system control bus (not shown) provides the interface from the host computer to the subsystems. A scan controller (not shown) provides real-time (acoustic vector rate) control inputs to the various subsystems. The scan controller is programmed by the host computer with the vector sequences and synchronization options for acoustic frame acquisitions. Thus, the scan controller controls the beam distribution and the beam density. The scan controller transmits the beam parameters defined by the host computer to the subsystems via a scan control bus (not shown).

The conventional system has the capability to superimpose graphical symbols on any ultrasound image. The superimposition of graphics on the image frame is accomplished in the video processor 14, which receives the ultrasound image frame from the X-Y display memory in the scan converter 12 and the graphics data from graphics/timeline display memory 18. The graphics data is processed and input into the graphics/timeline display memory 18 by the host computer 20 or, alternatively, by a dedicated graphics processor which is synchronized with the other subsystems by the host computer. The host computer is programmed to monitor the position of a trackball manipulated by the system operator on the operator interface, acquire spectral Doppler imaging data from a sample volume determined by the trackball position, and superimpose a sample gate cursor on the displayed image frame at a location corresponding to the trackball position. Similarly, the host computer is programmed to monitor the state of a toggle switch on the operator interface and to control the size of the sample volume (and the sample gate cursor) as a function of the state of the toggle switch.

Figure 2:
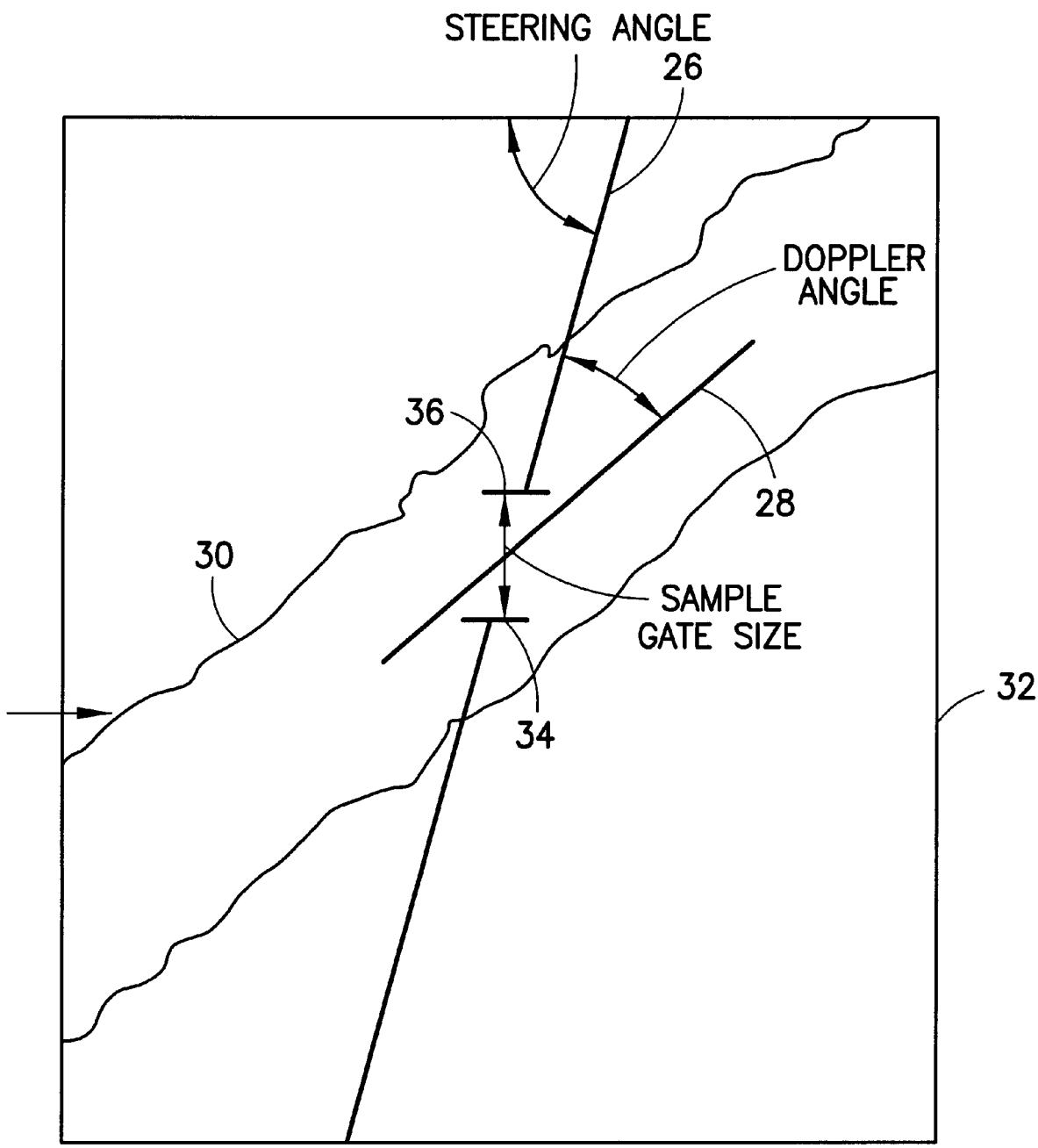
FIG. 2 is a schematic depicting an ultrasound image of a portion of a blood vessel with a sample gate graphic, a Doppler beam cursor and a vessel slope cursor superimposed thereon.

In accordance with the preferred embodiment of the invention, the Doppler sample gate position and size, as well as the beam steering angle, are automatically set based on actual vessel image data. This automatic adjustment can be performed either when the sample gate cursor is first activated or brought up in the image (before or upon spectral Doppler mode activation); or when the sample gate cursor is being moved by the system operator. FIG. 2 represents an image frame 32 produced by the system shown in FIG. 1. The exemplary image shown in frame 32 includes a visual representation of a blood vessel 30 with conventional graphics superimposed thereon. The displayed graphics include: a Doppler beam cursor (beam centerline) 26; a vessel slope cursor 28; and Doppler sample gate (sample volume) graphic, consisting of a sample gate top graphic 36 and a sample gate bottom graphic 34. In the latter type of sample gate graphic, the size of the sample gate is represented by the distance separating the bottom graphic 34 and the top graphic 36 in FIG. 2. However, it will be readily appreciated by persons skilled in the art that the sample gate graphic may have a different geometry, in which case the size of the sample gate would correspond to a dimension of such graphic, e.g., a diameter if the graphic were a circle. The estimated value of the Doppler angle between the Doppler beam cursor 26 and the vessel slope cursor 28 on the vessel 30 in the image 32 is used to convert Doppler frequency shifts into velocity units according to Eq. (1). The Doppler angle value is usually displayed along with the graphic.

In accordance with the preferred embodiment of the invention, the position and size of the sample volume (and the sample gate cursor formed by graphics 34 and 36) are set automatically by the ultrasound imaging system. In addition, the ultrasound imaging system can be programmed to select a steering angle which minimizes the Doppler angle, i.e., the angle between the beam steering direction and the vessel slope cursor.

Figure 3:
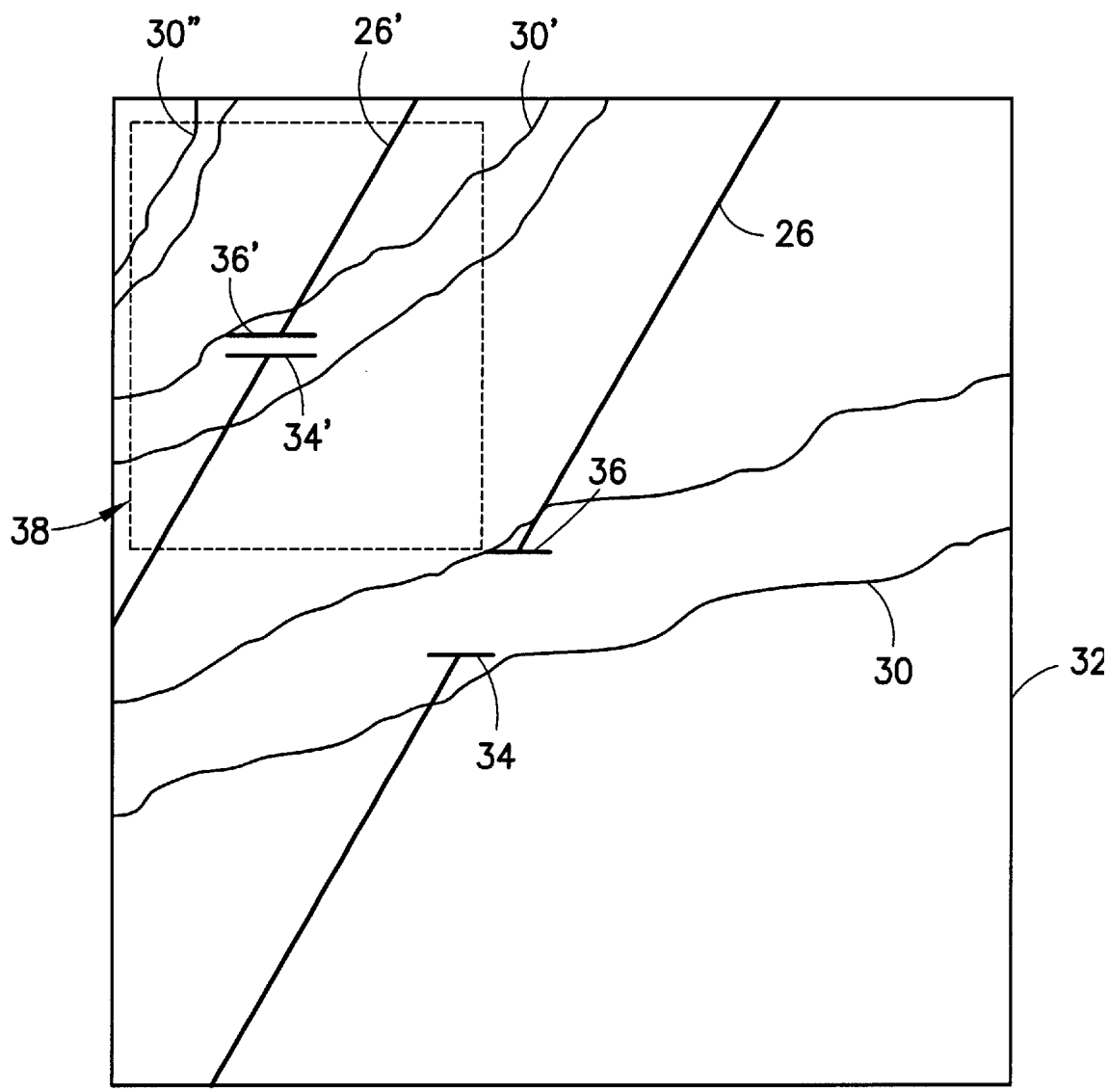
FIG. 3 is a schematic depicting an ultrasound image with a search region for sample gate re-selection shown as a dashed rectangle in one quadrant.

To set the sample volume or gate position automatically, the system first searches for the best vessel segment within the target search region. The target search region depends on the current Doppler operating condition. For the case when the sample gate cursor is first activated or brought up in the image (before or upon activation of the spectral Doppler imaging mode), the target search region may be a predetermined region of interest centered at a preset sample gate position. For the case when the sample gate cursor is being moved, the image quadrant (or a smaller sector) that the sample gate cursor is moving towards can be used to define the search region. For example, FIG. 3 shows a rectangular sector 38 in the upper left-hand quadrant of the image frame, toward which the sample gate cursor is moving. The image frame 32 shows portions of three vessels 30, 30' and 30". In accordance with one aspect of the preferred embodiment, the search region 38 is searched to find the best vessel segment therein. In this example, the best vessel segment, over which the re-selected sample gate is positioned, is a segment of vessel 30'. The re-selected sample gate is represented on the display screen by the sample gate bottom graphic 34' and the sample gate top graphic 36'.

In general, a target search region may contain more than one vessel segment. The "best" vessel segment can be chosen based on any reasonable morphological characteristic, such as the vessel diameter (closest to a standard size of the vessel type associated with the user-selected application type), greatest vessel length or area, or most uniform diameter (since the user usually moves the probe to obtain the best view of the vessel of interest), or a combination of goodness measures. Alternatively, the best vessel segment can be defined as the one which is at the shortest distance from the preset position (for the case when the sample gate cursor is first activated) or current sample gate position (for the case when the sample gate cursor is being moved).

Figure 4:
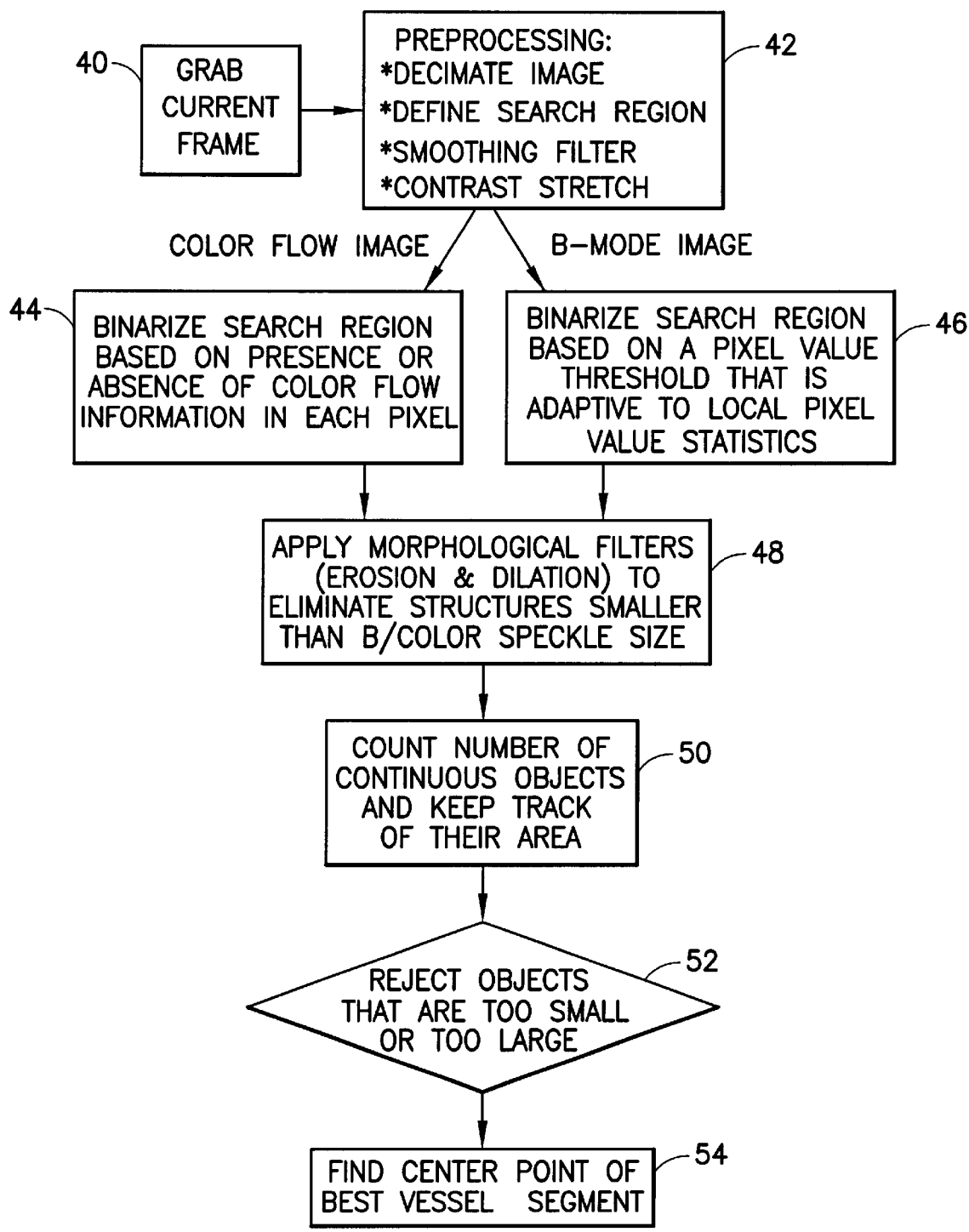
FIG. 4 is a flowchart showing an algorithm for automatic detection of vessel segments in accordance with the preferred embodiment of the invention.

To identify the best vessel segment within the search region, the algorithm shown in FIG. 4 is used. In a typical scanner, the current image frame can be read (step 40) either from the X-Y display memory in the scan converter or from the cine memory. To facilitate the vessel segment detection process, the image is first subject to some preprocessing (step 42), which may include any or all of the following: (1) image decimation to reduce the image to a smaller two-dimensional array of pixel elements; (2) definition of a search region within the decimated image; (3) application of a smoothing filter (e.g., median or mean filter) to reduce speckle noise; and (4) pixel intensity histogram equalization to enhance contrast between background and vessel ("contrast stretch" in block 42 in FIG. 4). The image decimation factor (e.g., 2) is in general dependent on a predefined minimum vessel size and the image size (in terms of pixel count) for the current image depth setting.

Still referring to FIG. 4, an adaptive thresholding method is used to binarize the search region (step 46) during B-mode imaging. The objective is to segment the search region by marking each pixel as either "1" if it is inside a cystic structure or "0" if it is not. Assuming that blood flow is hypoechoic, whereas soft tissues have relatively great pixel intensities, segmentation is achieved by comparing the intensity of each pixel to a threshold. In the simplest implementation, the threshold may be chosen based on some fraction of the global maximum intensity in the search region. For more robust performance, however, an adaptive scheme is also proposed wherein a threshold based on the local pixel intensity distribution is used to classify each pixel.

Figure 5:
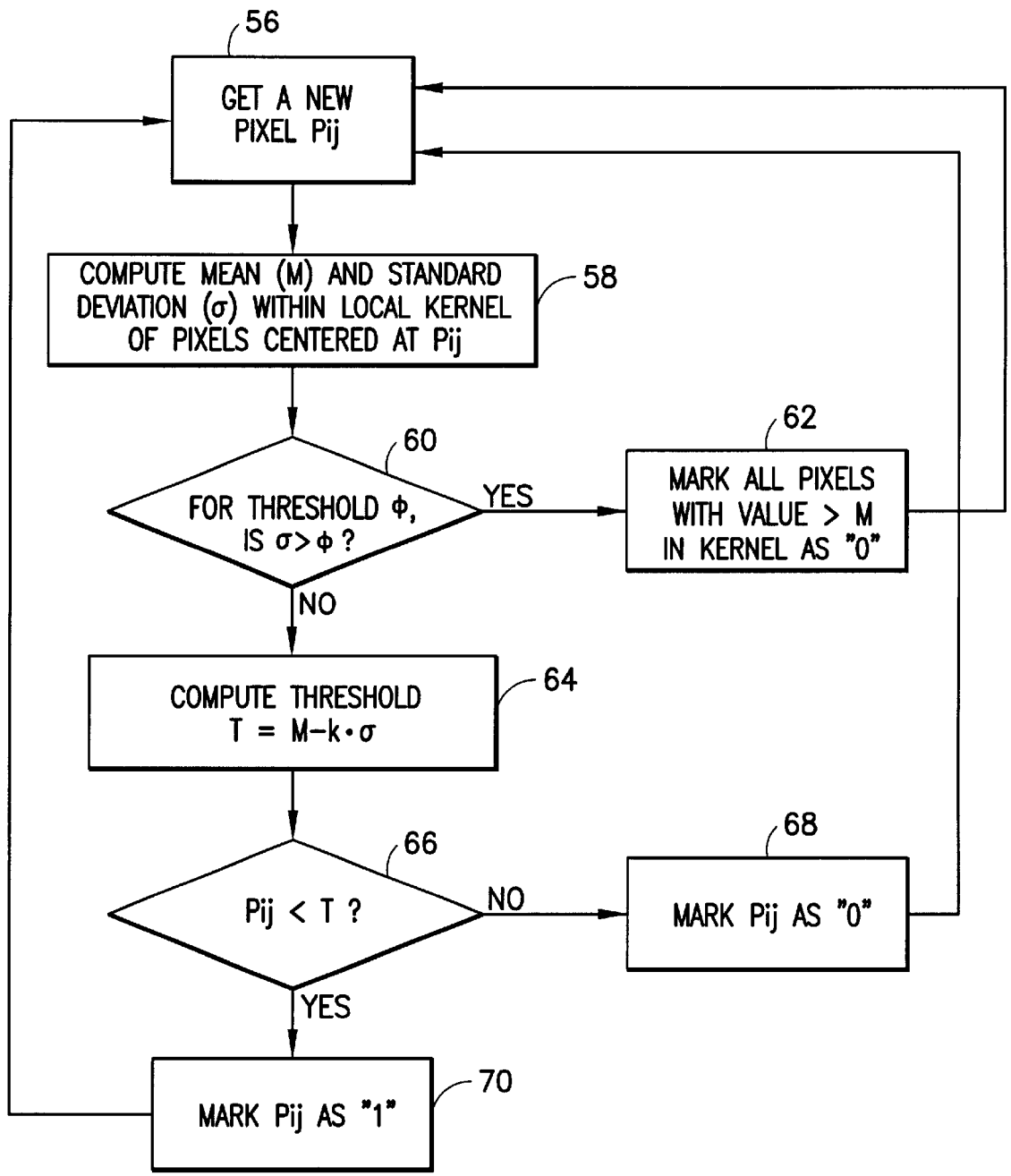
FIG. 5 is a flowchart showing an algorithm for binarization of the search region in accordance with the preferred embodiment of the invention.

While many variations of adaptive thresholding schemes are possible, a preferred binarization method for B-mode imaging is shown in FIG. 5. For each new pixel $P_{ij}$ in the search region (step 56), we first compute the local mean (M) and standard deviation ($\sigma$) of the neighboring pixels within an R×R kernel centered at pixel $P_{ij}$ (step 58). The kernel size R (e.g., 9) is chosen to be a little smaller than the expected minimum vessel size.

To test if the kernel contains only tissue speckle and is not inside a vessel, the standard deviation $\sigma$ is compared to a pre-defined threshold value $\phi$ (step 60). If $\sigma > \phi$, the pixels in the kernel are highly unlikely to be "blood flow"; however, if the kernel is partially inside a vessel, the condition of $\sigma > \phi$ may still hold. Therefore, only pixels in the kernel with a value greater than the mean (M) are marked as "1" (step 62). If σ<φ, an adaptive threshold T is computed (step 64) as follows:

$$T = M - k \times \sigma \quad (2)$$

where k is a constant. In general, k is a small positive fraction such as 0.2.

If $P_{ij}<T$ (step 66 in FIG. 5), then $P_{ij}$ is marked as "0" (not blood flow) (step 68); otherwise it is marked as "1" (blood flow) (step 70). The same marking step is repeated for each unmarked pixel in the search region (return to step 56).

For best performance, both B-mode and color flow (velocity or power) image data should be used. If color mode is not turned on, a hidden color frame can be fired just for this purpose. The advantages of using a color image are that it usually represents a clearer image of vessels with flowing blood, and it is already segmented to highlight the vessel lumen with flow. That is, the colorized pixels can be directly treated as the 1's in a binarized image mask (step 44 in FIG. 4). The rest of the processing (object counting and characterization) is then the same as for B-mode data. Depending on which set of data provides more clear image segmentation (more clear images of vessel segments), the decisive vessel morphology or distance measurements can be based on either or both of the B-mode and color flow data.

In general, the binarized image after adaptive thresholding may be very "noisy," consisting of many small, isolated structures. These small structures (mostly speckle noise) can be eliminated by using morphological filters (step 48 in FIG. 4), which are nonlinear image transformation techniques taught in many digital image processing textbooks (see, e.g., William K. Pratt, Digital Image Processing, 2nd edition, Wiley, N.Y.). Basic morphological operations can be implemented by direct pattern-matching ("hit or miss") transformations, or by using a more efficient pixel stacker and look-up table method.

Erosion and dilation represent two basic morphological operations which, when used in series, can be quite effective in closing up the speckle noise structures. Basically, each pass of an erosion filter strips off the outermost pixel layer of a continuous bright ("1") region. This tends to close up the small extraneous bright structures, like speckle noise. The erosion operation will also erode the outermost layer of any blood flow region. To offset this undesirable effect, an opposite operation, called a dilation, can be applied after each pass of an erosion filter. The effect of a dilation filter is to add back a layer of pixels to existing bright objects. Speckle noise gaps which have been completely closed up (no longer exist) by erosion filtering will not be regenerated by the dilation filter. In practice, one pass of the erosion filter followed by a dilation filter can eliminate a majority of speckle noise structures. But if necessary, additional passes of erosion and dilation can be performed.

The aim of step 50 in FIG. 4 is to count the total number of continuous objects in the morphologically filtered search region. A continuous object is defined as a set of object pixels ("1" s) that are connected to each other by pixels within the set. In general, a continuous object may contain holes or rough boundary pixel layers with small extrusions. These irregularities can cause confusion during the object segmentation process. Therefore, in accordance with the preferred embodiment of the invention, it is assumed that the objects of interest (vessels) have relatively well-defined shapes without extremely large holes or extrusions. The objective is to segment or group all the object pixels ("1"s) into distinct objects with different object numbers.

A computationally efficient approach that should work well in most situations is the following. Suppose $P_{ij}$ denotes the binarized pixel value in row i and column j. Beginning from one corner of the search region (e.g., $P_{00}$), the pixels in the image are checked and assigned an object number in a sequential manner as in a raster scan (i.e., row by row). If $P_{ij}=0$ (not blood flow), then it remains as zero. If $P_{ij}=1$ (blood flow), a predefined kernel of neighboring pixels, which have already been scanned, is reviewed. If at least one pixel in this neighborhood kernel is numbered as an object, then the current pixel is considered part of the same object and is assigned the same number. Otherwise, the current pixel is considered the beginning of a new object and is assigned a new object number. The neighborhood kernel consists of pixels in the previous column and/or previous row (which have already been scanned), i.e., pixels in row i, columns j−1, j−2, j−3, . . . , j−n, and row i−1, columns j−1, j, j+1, j+2, . . . , j+m,, where n and m are integer values. At a minimum, the pattern should include the three immediate neighbors $P_{i,j-1}$, $P_{i-1,j-1}$, $P_{i-1,j}$, which have already been scanned. The checking of additional pixels in the previous row/columns is recommended to help distinguish between small extrusions and/or broken fragments of an object already numbered and the beginning of a new object.

Having assigned numbers to all of the objects, the total number of objects can be counted easily. Also, the area of each object can be computed simply by counting the number of the pixels marked with a given object number.

Still referring to FIG. 4, in step 52 objects that are too large or too small are screened out. Although in step 48 morphological filters were used to remove small speckle-like structures, some of them may still be present in the search region. These small structures will now have unique object numbers, but they can be eliminated by checking whether their area is within a predefined range. If the area is smaller than some lower threshold (based on the mean speckle size of the scanner for the current imaging setup), it will be rejected. For example, a two-pixel object (Area=2 pixels) representing residual speckle noise will be rejected if the lower threshold is set at Area=3 pixels. If the counted area of an object is too large to be the interior of a vessel, the object will also be rejected. Only the remaining objects are considered to be "true" blood flow.

Following the rejection of objects having a size outside predetermined limits, the system automatically determines the "best" vessel segment in accordance with one of the goodness measures previously described and then calculates the center point of that vessel segment. Although not shown in FIGS. 2 and 3, a curved blood vessel, when intersected by the scan plane, may appear in the image as a discrete object within the frame boundaries, rather than as an object which traverses the frame from one edge to another. In the either case, the center point can be determined in various ways. For example, in step 54 (see FIG. 4) the x and y coordinates of the vessel center can be computed by simply taking the average values of the vessel boundaries along the horizontal and vertical axes, respectively. Other measures such as center-of-mass can also be used. For example, the "center of mass" of each remaining object could be computed using the following equations:

$$x_0 = \frac{\sum_{i=1}^{N} x_i}{N} \quad (3)$$

-continued $$y_0 = \frac{\sum_{i=1}^{N} y_i}{N} \quad (4)$$

In Eqs. (3) and (4), $x_0$ and $y_0$ are the coordinates of the center of mass of the object, N is the number of the pixels comprising the object, and $x_i$ and $y_i$ are the row and column coordinates for pixel $P_{ij}$.

Having identified the center of the best vessel segment, the vessel diameter and orientation can be computed using any automated method. For example, the automated methods for measuring the Doppler angle taught in either U.S. Pat. No. 5,690,116 or 6,068,598 could be used. The method taught in the latter prior art reference will be described here with reference to FIGS. 6–8.

Figure 6:
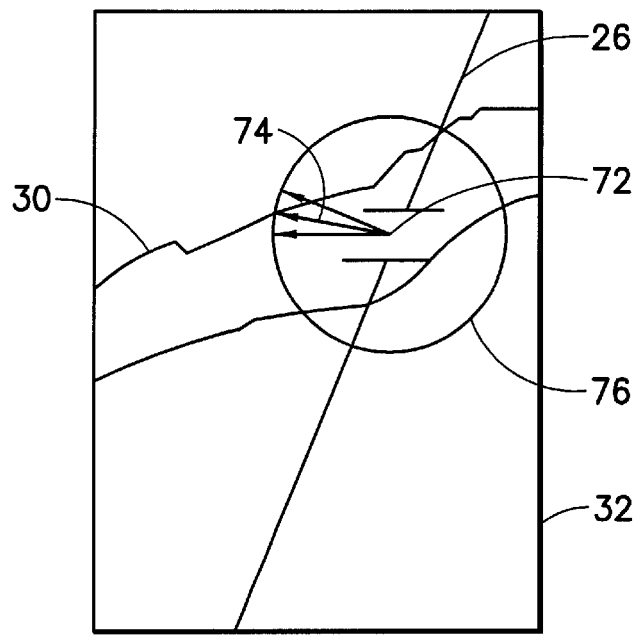
FIG. 6 is a schematic depicting an ultrasound image of a portion of a blood vessel with edge point search information superimposed thereon.
Figure 7:
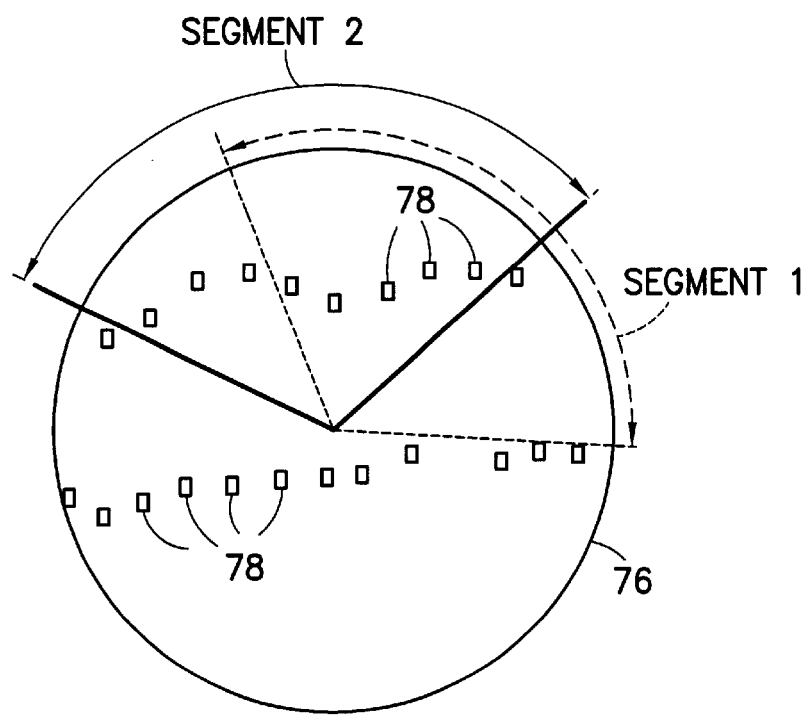
FIG. 7 is a schematic depicting segmentation of the edge points in accordance a method for automated estimation of the Doppler angle.

Referring to FIG. 6, the data representing the center point of the "best" vessel segment is identified by the host computer as the center point 72 of a search region 76. Based on the B-mode and color flow image data found within the search area 76, a Doppler angle is computed.

Figure 8:
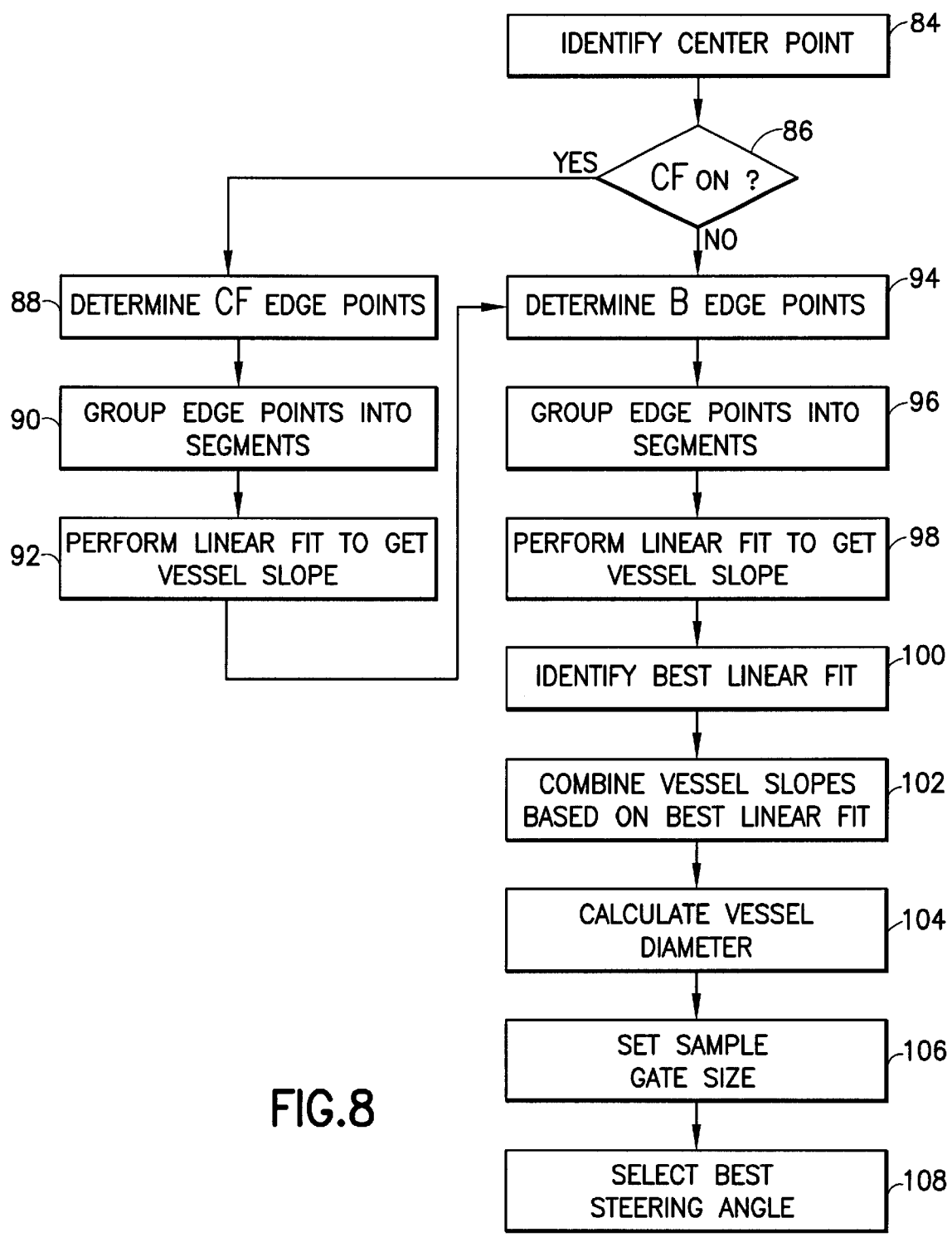
FIG. 8 is a flowchart depicting the algorithm for automatically adjusting the vessel slope cursor in accordance with a method for automated estimation of the Doppler angle.

Referring to FIG. 8, after the center point of the search region has been identified (step 84), the host computer determines (step 86) whether the image frame includes color flow data at pixel addresses corresponding to the location of the center point. If the image frame includes color flow data corresponding to the center point, then the host computer searches out from the center point 72 along radial lines 74 which are angularly spaced S degrees apart over an entire 360° range, as shown in FIG. 6. The distance to search from the center is D cm. This edge search area is indicated by circle 76 in FIGS. 6 and 7.

Along each radial line 74, the host computer searches from the center point 72 and stores the point as an edge point if it is the first of X points displaying B-mode intensity data instead of color flow velocity or power data (step 88 in FIG. 8). Exemplary edge points are depicted as rectangles 78 in FIG. 7. If no such point is found before searching D cm or finding the edge of the color region of interest, then no edge point is marked along that radial line. Once each radial line is searched, all the edge points 78 in a certain segment of the edge point search area (e.g., Segment 1 indicated by dotted lines in FIG. 7) are grouped together (step 90) and fed to a line-fit algorithm which generates both a vessel slope estimate and a goodness-of-fit measurement (step 92). This is repeated for other segments (e.g., Segment 2 indicated by solid straight lines in FIG. 7) and in each case the slope of the vessel and the goodness of fit are recorded. The segments may overlap each other by some number of degrees, as do Segments 1 and 2 shown in FIG. 7. If a particular segment does not have some minimum number of edge points within it, then that segment is disregarded.

In addition to the foregoing, the algorithm also determines B-mode edge points (step 94) by searching the B-mode intensity data from the center point in radial lines spaced S degrees apart over an entire 360° range. The distance to search from the center is D cm. Along each radial line each B-mode intensity value (corresponding to respective pixels) is replaced with the average of itself and its two neighbors along the radius. The peak and minimum intensities along the averaged radial line as well as the largest difference (from one pixel to the next) are each recorded. If the difference between the peak and minimum intensities does not exceed some threshold, then no edge point is specified for this ray. If the difference between the peak and minimum intensities exceeds the threshold, then a search is started at some number of points from the center and stops when a point (the edge point) is found to exceed a difference-only threshold, an intensity-only threshold or a combined difference and intensity threshold. For example, if the pixel location is 50% of the maximum intensity and 30% of the maximum difference, then it would pass the combined difference and intensity threshold. The intensity at the edge point is noted. If no such point is found before searching D cm or finding the edge of the B-mode image, then no edge point is marked along that radial line. Once each radial line has been searched, some percent of the edge points are disregarded. The disregarded edge points are those associated with the lowest intensities. All of the remaining edge points in a certain segment of the edge point search area are grouped (step 96) and then fed to a line-fit algorithm which generates both a vessel slope estimate and a goodness-of-fit measurement (step 98). This is repeated for other segments, and in each case the vessel slope and the goodness of fit are recorded. The segments may overlap each other by some number of degrees. If a particular segment does not have some minimum number of edge points within it, then that segment is disregarded.

If no B-mode or color flow mode segment generated enough edge points to get a vessel slope estimate, the distance D is increased and the algorithm is rerun.

At this point in the algorithm, estimates of the vessel slope and their corresponding goodness-of-fit measurements are known for some number of segments (for B mode and color flow mode). The segment having the best goodness of fit is identified (step 100) and its vessel slope is combined (averaged) with all the other vessel slope estimates that have a goodness of fit measurement not exceeding some difference relative to the best one (step 102). However, if color is active and the best color vessel slope exceeds some number of degrees (indicating a vessel somewhat vertical), then only color data is used in this vessel slope-combining algorithm. This is done because somewhat vertical vessel walls are difficult to detect in B-mode due to the lateral smearing of the image data. The host computer determines the vessel diameter (step 104 in FIG. 8) by calculating the distance between edge points along a line passing through the center point and orthogonal to the calculated vessel slope.

After the vessel diameter and orientation have been computed, the sample gate size can be automatically set (step 106 in FIG. 8) to be some fraction of the vessel diameter. The optimal fraction can be pre-selected based on the practice of the individual clinical site. It does not have to be 100% or greater, since the typical Doppler exam is aimed at detecting arterial diseases and not for volume flow measurement.

Alternatively, if power Doppler image of the vessel is available, the sample gate size adjustment can be based on power Doppler intensity levels within the vessel lumen. This technique makes use of the fact that the power Doppler intensity usually varies from zero near the vessel wall to maximum brightness towards the center of the vessel. For example, the sample gate boundaries can be placed at the −10 dB drop-off points from the maximum in the power Doppler image of the vessel lumen.

Finally, having established the vessel orientation based on image analysis, the best steering angle can be chosen automatically (step 108 in FIG. 8) to minimize the Doppler angle. For example, if the imaging system is programmed with multiple sets of beamforming time delay tables corresponding to multiple beam steering angles, the host computer need only determine which beam steering angle is closest to the vessel slope calculated based on image analysis, i.e., by identifying which beam steering angle minimizes the difference between the beam steering angle and the vessel orientation angle.

Although the preferred embodiment has been disclosed in the context of an ultrasound imaging system having a host computer which processes graphics, a separate dedicated graphics processor can be employed which is separate from the host computer. Furthermore, although FIG. 1 shows the architecture of an ultrasound imaging system having multiple processors and a host computer, all of the data processing and computing functions could be performed by a single computer having sufficient processing power.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A method of locating a sample gate in a test subject, comprising the steps of:
    (a) detecting a predetermined state associated with a sample gate graphic superimposed on an image being displayed;
    (b) processing a frame of imaging data from which said image was derived to determine a predetermined point in a vessel segment in said test subject in response to detection of said predetermined state;
    (c) moving a sample gate to a predetermined position relative to said predetermined point in response to completion of said processing step; and
    (d) superimposing a sample gate graphic at a new position in said image, said new position corresponding to said predetermined position of said sample gate.

2. The method as recited in claim 1, further comprising the steps of:
    (d) processing said imaging data to determine a dimension of said vessel segment; and
    (e) adjusting a dimension of said sample gate to have a predetermined relationship to said dimension of said vessel segment.

3. The method as recited in claim 2, wherein said dimension represents an internal diameter of said vessel segment.

4. The method as recited in claim 1, wherein said predetermined state comprises activation of said sample gate graphic.

5. The method as recited in claim 1, wherein said predetermined state comprises movement of said sample gate graphic.

6. The method as recited in claim 1, wherein said step (b) comprises the steps of:
    defining a search region in said image; and
    searching said search region for a continuous object representing a vessel segment having a predetermined morphological characteristic,
    wherein said sample gate graphics is placed in predetermined relationship to a center point of said continuous object representing said vessel segment having said predetermined morphological characteristic.

7. The method as recited in claim 6, wherein said searching step comprises the step of binarizing the pixel values within said search region.

8. The method as recited in claim 7, wherein said binarizing step comprises the step of binarizing the pixel values based on a pixel value threshold that is adaptive to local pixel value statistics.

9. The method as recited in claim 7, wherein said binarizing step comprises the step of binarizing the pixel values based on the presence versus absence of color flow information in each pixel.

10. The method as recited in claim 7, wherein said searching step further comprises the step of performing morphological filtering to eliminate structures smaller than a speckle size.

11. The method as recited in claim 10, wherein said searching step further comprises the steps of:
    counting the number of continuous objects in said search region;
    computing the area of each continuous object; and
    rejecting objects having an area lying outside a predetermined range.

12. The method as recited in claim 1, further comprising the steps of:
    (d) processing said imaging data to determine an angle of orientation of said vessel segment in said image; and
    (e) selecting a beam steering angle from a plurality of predefined beam steering angles which minimizes an angle between said angle of orientation of said vessel segment and said beam steering angle.

13. The method as recited in claim 1, wherein step (b) comprises the step of finding a center of mass of said vessel segment.

14. The method as recited in claim 1, wherein step (b) comprises the step of calculating average values of a boundary of said vessel segment along horizontal and vertical axes.

15. The method as recited in claim 2, wherein said step (e) is based on power Doppler intensity levels acquired for pixels within said vessel segment.

16. A method of sizing a sample gate in a test subject, comprising the steps of:
    (a) detecting a predetermined state associated with a sample gate graphic being displayed;
    (b) processing a frame of imaging data from which said image was derived to determine a dimension of a vessel segment in said test subject in response to detection of said predetermined state;
    (c) adjusting a dimension of said sample gate to have a predetermined relationship to said dimension of said vessel segment in response to completion of said processing step; and
    (d) superimposing a sample gate graphic on said image, said sample gate graphic having a dimension corresponding to said adjusted dimension of said sample gate.

17. The method as recited in claim 16, wherein said dimension of said continuous object represents an internal diameter of said vessel segment.

18. A system comprising:
    a display device comprising a multiplicity of pixels;
    a memory for storing a frame of image pixel values; and
    a computer programmed to perform the steps of:
    (a) controlling said display device to display an image derived from said frame of image pixel values and a sample gate graphic superimposed on said image;
    (b) detecting a predetermined state associated with said sample gate graphic being displayed;

(c) processing said image pixel values to determine a predetermined point in a vessel segment in said test subject in response to detection of said predetermined state;

(d) moving a sample gate to a predetermined position relative to said predetermined point in response to completion of said processing step; and (e) superimposing a sample gate graphic at a new position in said image, said new position corresponding to said predetermined position of said sample gate.

19. The system as recited in claim 18, wherein said computer is further programmed to perform the following steps:

(f) processing said image pixel values to determine a dimension of said vessel segment; and (g) adjusting a dimension of said sample gate graphic so that it has a predetermined relationship to said dimension of said vessel segment.

20. The system as recited in claim 19, wherein said dimension represents an internal diameter of said vessel segment.

21. The system as recited in claim 18, wherein said predetermined state comprises activation of said sample gate graphic.

22. The system as recited in claim 18, wherein said predetermined state comprises movement of said sample gate graphic.

23. The system as recited in claim 18, wherein said computer is further programmed to perform the following steps:

defining a search region in said image; and searching said search region for a continuous object representing a vessel segment having a predetermined morphological characteristic, wherein said sample gate graphics is placed in predetermined relationship to a center point of said continuous object representing said vessel segment having said predetermined morphological characteristic.

24. The system as recited in claim 23, wherein said searching step comprises the step of binarizing the pixel values within said search region.

25. The system as recited in claim 24, wherein said binarizing step comprises the step of binarizing the pixel values based on a pixel value threshold that is adaptive to local pixel value statistics.

26. The system as recited in claim 24, wherein said binarizing step comprises the step of binarizing the pixel values based on the presence versus absence of color flow information in each pixel.

27. The system as recited in claim 24, wherein said searching step further comprises the step of performing morphological filtering to eliminate structures smaller than a speckle size.

28. The system as recited in claim 27, wherein said searching step further comprises the steps of:

counting the number of continuous objects in said search region;

computing the area of each continuous object; and rejecting objects having an area lying outside a predetermined range.

29. The system as recited in claim 18, wherein said computer is further programmed to perform the following steps:

(f) processing said imaging data to determine an angle of orientation of said vessel segment; and (g) selecting a beam steering angle from a plurality of predefined beam steering angles which minimizes an angle between said angle of orientation of said vessel segment and said beam steering angle.

30. The system as recited in claim 18, wherein step (c) comprises the step of finding a center of mass of said vessel segment.

31. The system as recited in claim 18, wherein step (b) comprises the step of calculating average values of a boundary of said vessel segment along horizontal and vertical axes.

32. The system as recited in claim 19, wherein said step (f) is based on power Doppler intensity levels acquired for pixels within said vessel segment.

33. The system as recited in claim 18, further comprising:

an ultrasound transducer array comprising a multiplicity of transducer elements;

a transmit beamformer for pulsing selected transducer elements to transmit a series of ultrasound transmit beams in a scan plane;

a receive beamformer coupled to selected transducer elements of said transducer array for acquiring respective receive signals subsequent to respective beam transmits;

a signal processor for forming vectors of image parameter values from said receive signals; and a scan converter for converting said vectors into a frame of image pixel values and storing said frame of image pixel values in said memory.

34. A system comprising:

a display device comprising a multiplicity of pixels;

a memory for storing a frame of image pixel values; and a computer programmed to perform the steps of:

(a) controlling said display device to display an image derived from said frame of image pixel values and a sample gate graphic superimposed on said image;

(b) detecting a predetermined state associated with said sample gate graphic being displayed;

(c) processing said image pixel values to determine a dimension of a vessel segment in said test subject in response to detection of said predetermined state;

(d) adjusting a dimension of said sample gate to have a predetermined relationship to said dimension of said vessel segment in response to completion of said processing step; and (e) superimposing a sample gate graphic on said image, said sample gate graphic having a dimension corresponding to said adjusted dimension of said sample gate.

35. The system as recited in claim 34, wherein said dimension represents an internal diameter of said vessel segment.

36. A system comprising:

a display device;

a memory for storing a frame of image pixel values;

means for controlling said display device to display an image derived from said frame of image pixel values;

means for controlling said display device to display a sample gate graphic superimposed on said image;

means for detecting a predetermined state associated with said sample gate graphic being displayed;

means for processing said image pixel values to determine a predetermined point in a vessel segment in said test subject in response to detection of said predetermined state;

means for moving a sample gate to a predetermined position relative to said predetermined point in response to completion of said processing step; and means for controlling said display device to superimpose a sample gate graphic at a new position in said image, said new position corresponding to said predetermined position of said sample gate.

37. The system as recited in claim 36, further comprising:

means for processing said imaging data to determine a dimension of said vessel segment; and means for adjusting a dimension of said sample gate graphic to have a predetermined relationship to said dimension of said vessel segment.

\* \* \* \* \*

UNITED STATES PATENT AND TRADEMARK OFFICE
CERTIFICATE OF CORRECTION

PATENT NO. : 6,322,509 B1
DATED : November 27, 2001
INVENTOR(S) : Lihong Pan et al.

Page 1 of 1

It is certified that error appears in the above-identified patent and that said Letters Patent is hereby corrected as shown below:

<u>Column 10,</u>
Line 21, insert -- P -- in front of the subscript "i-1, j-1".

Signed and Sealed this

Nineteenth Day of March, 2002

Attest:

Attesting Officer

JAMES E. ROGAN
Director of the United States Patent and Trademark Office